United States Patent
Sasazaki et al.

(10) Patent No.: US 9,827,142 B2
(45) Date of Patent: Nov. 28, 2017

(54) TIP FOR PHACOEMULSIFICATION

(71) Applicant: JMR CO., LTD., Niigata-shi, Niigata (JP)

(72) Inventors: Atsushi Sasazaki, Niigata (JP); Shinya Oganna, Hatsukaichi (JP)

(73) Assignee: JMR CO., LTD., Niigata-shi, Niigata (JP)

( * ) Notice: Subject to any disclaimer, the term of this patent is extended or adjusted under 35 U.S.C. 154(b) by 212 days.

(21) Appl. No.: 14/891,360

(22) PCT Filed: May 20, 2014

(86) PCT No.: PCT/JP2014/063298
§ 371 (c)(1),
(2) Date: Nov. 16, 2015

(87) PCT Pub. No.: WO2014/192584
PCT Pub. Date: Dec. 4, 2014

(65) Prior Publication Data
US 2016/0067089 A1    Mar. 10, 2016

(30) Foreign Application Priority Data

May 28, 2013   (JP) .............................. 2013-002969 U

(51) Int. Cl.
*A61F 9/00*   (2006.01)
*A61F 9/007*  (2006.01)

(52) U.S. Cl.
CPC ...... *A61F 9/00736* (2013.01); *A61F 9/00745* (2013.01)

(58) Field of Classification Search
CPC ............. A61F 9/00745; A61F 9/00736; A61B 2217/005; A61B 2010/0208;
(Continued)

(56) References Cited

U.S. PATENT DOCUMENTS 5,451,229 A      9/1995  Geuder et al.
5,989,209 A *   11/1999  Barrett ................ A61F 9/00745
                                                              604/22
(Continued)

FOREIGN PATENT DOCUMENTS

JP    H08-038541 A    2/1996
JP    2006-000644 A   1/2006
JP    2006-247392 A   9/2006

OTHER PUBLICATIONS

International Search Report for PCT/JP2014/063298 dated Aug. 12, 2014.
PCT written openion dated Aug. 12, 2014.

*Primary Examiner* — Diane Yabut
*Assistant Examiner* — Erich Herbermann
(74) *Attorney, Agent, or Firm* — Yokoi & Co., U.S.A.; Toshiyuki Yokoi

(57) ABSTRACT

Provided is a tip for phacoemulsification superior in ability to efficiently and smoothly crush and suck a crystalline lens. A tip (1) of the present invention includes: a shaft (2) having first and second ends (21, 22); a distal part (3) arranged at the first end (21) of the shaft (2) and having an opening (4); and a suction passage (5) extending from the opening (4) of the distal part (3) to the second end (22) of the shaft (2). The suction passage (5) is narrowed in a staircase shape (51) or/and a helical shape (53) from the opening (4) toward the shaft (2). It is preferable that one or a plurality of guide grooves (52) leading from the opening (4) toward the shaft (2) are further formed in an inner wall of the suction passage (5).

4 Claims, 5 Drawing Sheets

(58) Field of Classification Search
CPC .......... A61B 2010/045; A61B 10/0038; A61B 10/02; A61B 10/0283
USPC ......................................................... 604/22
See application file for complete search history.

(56) References Cited

U.S. PATENT DOCUMENTS

| | | | |
|---|---|---|---|
| 6,074,396 A * | 6/2000 | Geuder | A61F 9/00745 604/22 |
| 6,283,974 B1 | 9/2001 | Alexander | |
| 2006/0052758 A1 * | 3/2006 | Dewey | A61F 9/00745 604/272 |

\* cited by examiner

TIP FOR PHACOEMULSIFICATION

TECHNICAL FIELD

The present invention relates to a tip available for phacoemulsification that is a kind of ophthalmic surgery.

BACKGROUND ART

In a cataract operation, a surgical operation called phacoemulsification is generally performed in order to remove a cloudy crystalline lens of a patient. This operative procedure inserts a dedicated tip into the crystalline lens, vibrates the tip with an ultrasonic wave while supplying a perfusion fluid to crush and emulsify the crystalline lens, and sucks and eliminates the crushed and emulsified crystalline lens together with the perfusion fluid to the outside of a body via a suction passage in the tip.

As a publicly-known tip for phacoemulsification (also referred to simply as a "tip"), for example, structures disclosed in Patent Documents 1 and 2 are proposed.

However, the tip is demanded to be further improved in performance (increased in crushing force and improved in crushing efficiency) and has room for improvement.

PRIOR ART DOCUMENT

Patent Document

Patent Document 1: Japanese Patent Laid-open Publication No. 2006-000644

Patent Document 2: Japanese Patent Laid-open Publication No. 2006-247392

DISCLOSURE OF THE INVENTION

Problems to be Solved by the Invention

The present invention has been made in consideration of the above circumstances and its object is to provide a tip for phacoemulsification superior in ability to efficiently and smoothly crush and suck a crystalline lens.

Means for Solving the Problems

After repeating experimental production and test while recognizing that the shape and the structure of a distal part are extremely important in order to efficiently and smoothly crush and suck a crystalline lens, the present inventors have found a tip suitable for realizing the above-described object and reached completion of the present invention.

More specifically, the present invention employs, for example, the following configurations and features.

(Aspect 1)

A tip for phacoemulsification, comprising:

a shaft having first and second ends;

a distal part arranged at the first end of the shaft and having an opening; and a suction passage extending from the opening of the distal part to the second end of the shaft, wherein the suction passage is narrowed, at the distal part, in a helical shape from the opening toward the shaft.

(Aspect 2)

A tip for phacoemulsification, comprising:

a shaft having first and second ends;

a distal part arranged at the first end of the shaft and having an opening; and a suction passage extending from the opening of the distal part to the second end of the shaft, wherein the suction passage has, at the distal part, a first section provided on the opening side and a second section provided on the first end side of the shaft, wherein the suction passage is narrowed in a staircase shape toward the shaft, in the first section, and wherein the suction passage is narrowed in a helical shape toward the shaft, in the second section.

(Aspect 3)

A tip for phacoemulsification, comprising:

a shaft having first and second ends;

a distal part arranged at the first end of the shaft and having an opening; and a suction passage extending from the opening of the distal part to the second end of the shaft, wherein the suction passage has, at the distal part, a first section provided on the opening side and a second section provided on the first end side of the shaft, wherein the suction passage is narrowed in a helical shape toward the shaft, in the first section, and wherein the suction passage is narrowed in a staircase shape toward the shaft, in the second section.

(Aspect 4)

The tip for phacoemulsification according to any one of aspects 1 to 3, wherein one or a plurality of guide grooves leading from the opening toward the shaft are further formed in an inner wall of the suction passage.

(Aspect 5)

A tip for phacoemulsification, comprising:

a shaft having first and second ends;

a distal part arranged at the first end of the shaft and having an opening; and a suction passage extending from the opening of the distal part to the second end of the shaft, wherein the suction passage is narrowed, at the distal part, in a staircase shape from the opening toward the shaft, and wherein one or a plurality of guide grooves leading from the opening toward the shaft are further formed in an inner wall of the suction passage.

(Aspect 6)

The tip for phacoemulsification according to aspect 4 or 5, wherein a plurality of the guide grooves are formed in a manner to equally divide an outer periphery of the inner wall.

Effect of the Invention (Crushing and Fragmenting Function)

According to the tip of the present invention, the suction passage is structured to be narrowed in a staircase shape or/and a helical shape from the opening of the distal part toward the shaft and therefore causes the crushed substance of the crystalline lens sucked from the opening to collide with the above-described structure and thereby be more finely crushed, thus greatly improving the crushing efficiency of the tip.

(Function of Guiding and Flowing-Out to the Downstream Side (Stay Prevention Function))

Further, according to the tip of the present invention, one or a plurality of guide grooves leading from the opening toward the shaft are further formed in an inner wall of the suction passage constituting the above-described structure, thereby allowing the fluid containing the crushed substance of the crystalline lens which has collided with the above-described structure to smoothly flow out to the downstream side without staying near the structure.

Note that the helical shape structure described in any one of the above-described aspects 1 to 4 can realize, by the structure itself, both the above-described crushing and fragmenting function and the above-described function of guiding and flowing-out to the downstream side (stay prevention function) at the same time with respect to the sucked crushed substance of the crystalline lens.

On the other hand, the staircase shape structure described in the above-described aspect 5 or 6 can realize only the above-described crushing and fragmenting function by itself, and can impart also the above-described function of guiding (stay prevention) by further forming the above-described guide grooves in the inner wall of the suction passage.

Accordingly, employing any aspect of the present invention makes it possible to fully achieve both of the above-described functions and thereby provide a tip for phacoemulsification superior in ability to efficiently and smoothly crush and suck a crystalline lens, which is the above-described object of the present invention.

BEST MODE FOR CARRYING OUT THE INVENTION

Figure 1A:
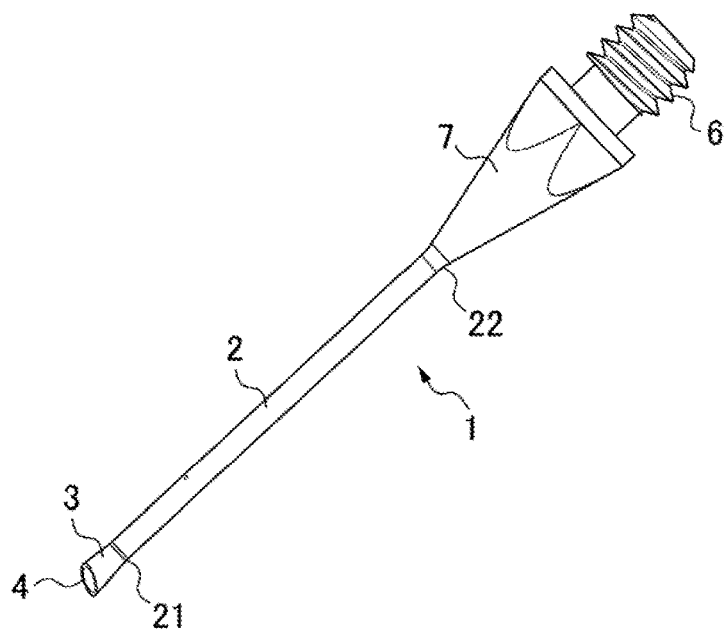
FIG. 1A is a perspective view illustrating a tip in Example 1.

Hereinafter, the present invention will be described on the basis of examples illustrated in the drawings, but the present invention is not limited at all to the following concrete examples. Note that the same numerals are used for the same or corresponding components in the drawings.

Example 1

(Tip in which Staircase Shape Stepped Structures and Guide Grooves are Arranged in a Suction Passage on a Distal Part Side)

Figure 1B:
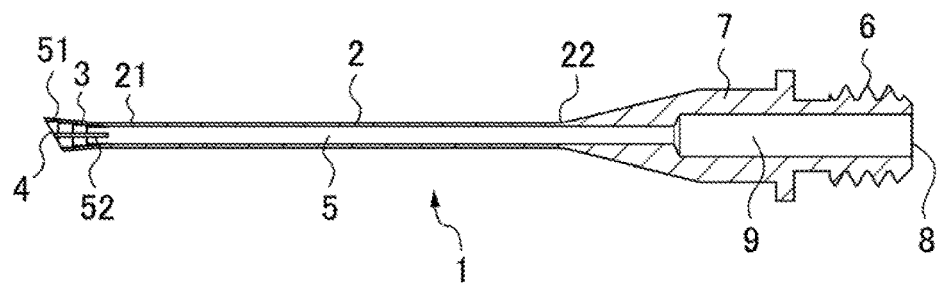
FIG. 1B is a cross-sectional view illustrating a tip in Example 1.
Figure 1C:
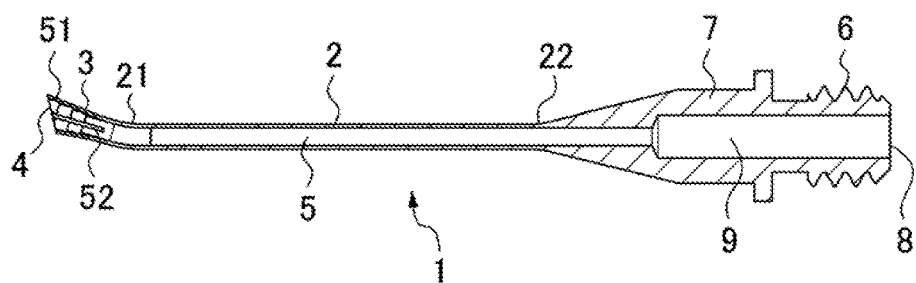
FIG. 1C is a cross-sectional view illustrating a tip in a modification Example 1.
Figure 2A:
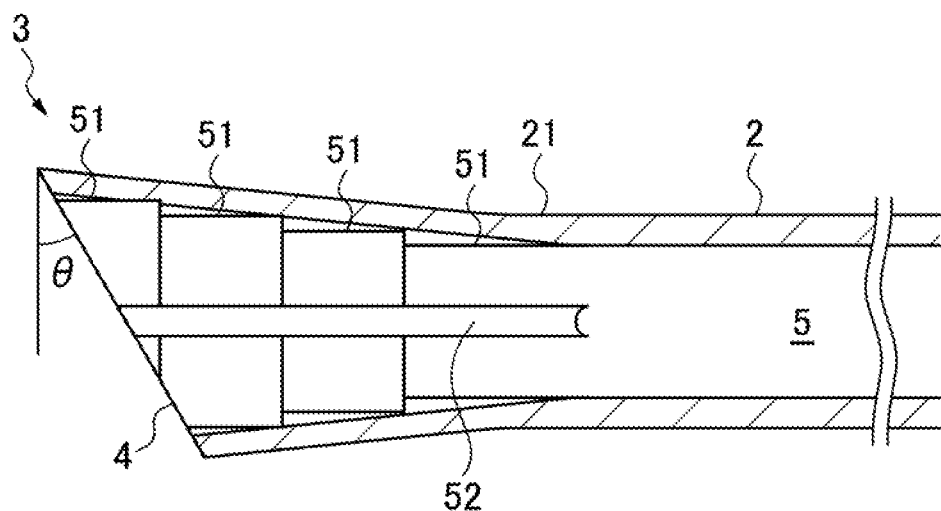
FIG. 2A is an enlarged cross-sectional view illustrating a distal part in Example 1.
Figure 2B:
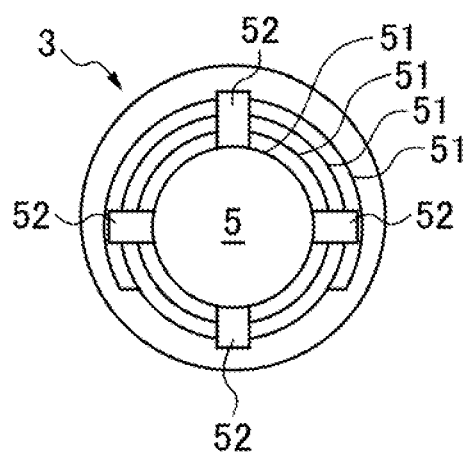
FIG. 2B is an enlarged side view illustrating a distal part in Example 1.

A tip 1 in Example 1 will be described referring to FIGS. 1A, 1B, 1C, 2A and 2B. FIGS. 1A and 1B are a perspective view and a cross-sectional view illustrating the tip 1 in Example 1. Note that FIG. 1C illustrates a later-described modification example of Example 1. Further, FIGS. 2A and 2B are enlarged cross-sectional and side views illustrating a distal part 3 in Example 1.

The tip 1 in Example 1 includes, as in the configuration of a publicly-known tip, a shaft 2 having first and second ends 21, 22, the distal part 3 arranged at the first end 21 of the shaft 2 and having an opening 4, and a suction passage 5 extending from the opening 4 of the distal part 3 to the second end 22 of the shaft 2. Note that the opening 4 of the distal part 3 may be diagonally cut to have an inclined angle θ as illustrated in FIG. 2A. A preferable inclined angle θ is $0° \leq θ \leq 45°$. A larger angle θ makes a crystalline lens become more likely to be broken by the opening. On the other hand, a smaller angle θ makes the crystalline lens become slightly less likely to be broken by the opening, but provides an advantage that the crystalline lens becomes more likely to be caught by the opening.

(Material of the Tip)

Note that as the material of the tip 1, a titanium alloy such as Ti-6Al-4V is preferable from the viewpoint of ductility, toughness, mechanical strength, machinability, and weldability, but the material is not necessarily limited to this, and other metals and resins may be used.

(Attachment of the Tip to Another Apparatus)

Besides, the tip 1 constitutes, together with a handpiece (not illustrated), one of components of a phacoemulsifier, and further includes a thread part 6 attachable and detachable to/from an ultrasonic device (not illustrated) in the handpiece, and a hub 7 connecting the above-described thread part 6 and shaft 2 (see drawings in FIGS. 1A, 1B and 1C). An end surface of the thread part 6 is provided with an opening 8, and the thread part 6 and the hub 7 are provided with a communication passage 9 communicating the opening 8 and the suction passage 5 so that a perfusion fluid (also referred to simply as "fluid") containing a crushed substance of the crystalline lens sucked from the opening 4 of the distal part 3 into the suction passage 5 passes through the handpiece and is then discharged to the outside of the phacoemulsifier.

(Suction Structure of the Suction Passage)

Here, it should be noted that, in Example 1, the suction passage 5 is narrowed in a staircase shape from the opening 4 toward the shaft 2 as indicated with numerals 51 in FIG. 2A. In the illustrated example, four hollow cylindrical flow channels different in inside diameter (becoming smaller in sequence) are formed in the suction passage 5 so that staircase shape structures 51 at four steps are formed in the cross-sectional view.

This causes the crushed substance of the crystalline lens (not illustrated) sucked from the opening 4 to collide with (steps generated by) the above-described staircase shape structures 51 and thereby be more finely crushed, thus greatly improving the crushing efficiency of the tip 1.

It also should be noted that one or a plurality of (four in the illustrated example) guide grooves 52 leading from the opening 4 toward the shaft 2 are further formed in an inner wall of the suction passage 5. This allows the fluid containing the crushed substance of the crystalline lens which has collided with the above-described staircase shape structures 51 to extremely smoothly flow out to the downstream side (the suction passage 5, the communication passage 9) without staying near the structures 51.

Note that it is preferable that a plurality of the guide grooves 52 are formed in a manner to equally divide the outer periphery of the inner wall. In the illustrated example, the grooves are arranged every 90° in a manner to divide the outer periphery (circumference) into four parts.

(Modification Example of the Distal Part)

The distal part 3 is premised to have a configuration that it is arranged on the same axis as the axis of the shaft 2 in the above-described Example 1, but is not necessarily limited to this configuration. For example, a configuration in which the distal part 3 is inclined to be curved with respect to the shaft 2 as illustrated in FIG. 1C, may be employed, and the above-described operation and effect of the present invention can be similarly obtained.

Example 2

(Tip in which Helical Shape Structures are Arranged in a Suction Passage on a Distal Part Side)

A tip 1 in Example 2 will be described referring to FIGS. 3A and 3B. The tip 1 in Example 2 has a suction passage 5 different in structure from that in Example 1 as will be described later, but its other components have substantially the same features and functions as those of the components described in Example 1 and therefore their description will be omitted here.

Figure 3C:
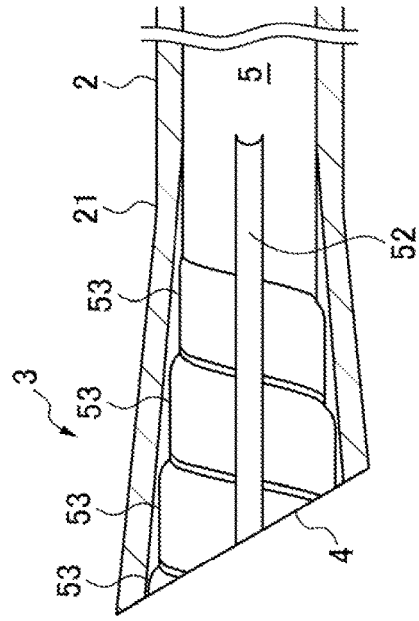
FIG. 3C is an enlarged cross-sectional view illustrating a distal part in Example 3.
Figure 3D:
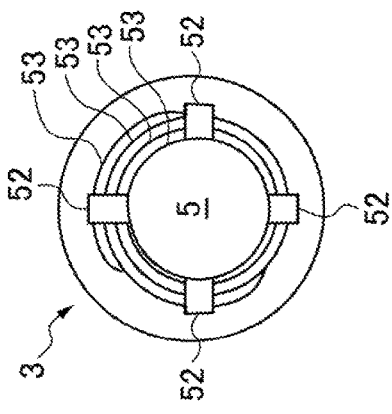
FIG. 3D is an enlarged side view illustrating a distal part in Example 3.
Figure 3A:
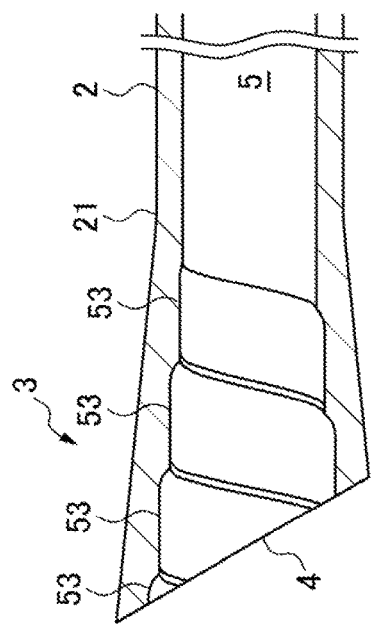
FIG. 3A is an enlarged cross-sectional view illustrating a distal part in Example 2.
Figure 3B:
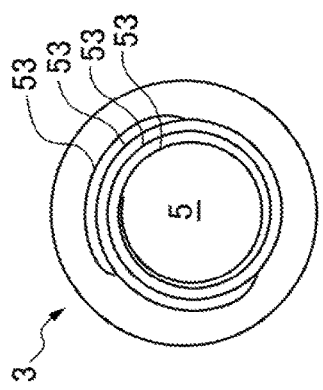
FIG. 3B is an enlarged side view illustrating a distal part in Example 2.
Figure 4A:
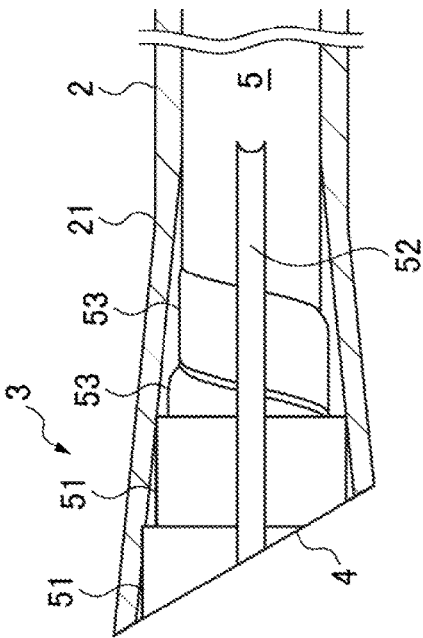
FIG. 4A is an enlarged cross-sectional view illustrating a distal part in Example 4.
Figure 4B:
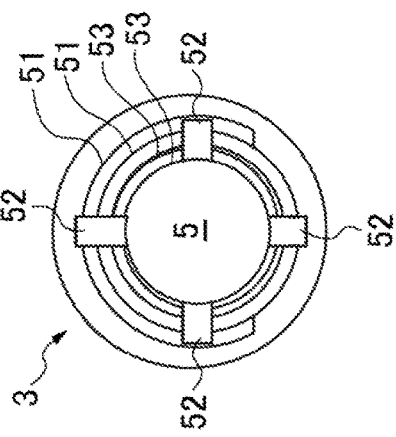
FIG. 4B is an enlarged side view illustrating a distal part in Example 4.
Figure 4C:
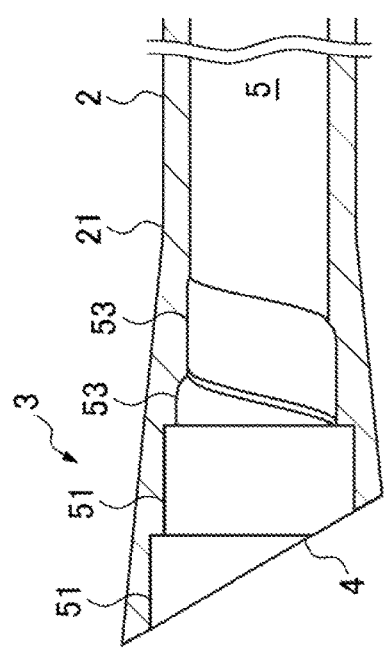
FIG. 4C is an enlarged cross-sectional view illustrating a distal part in the combination of Example 3 and Example 4.
Figure 4D:
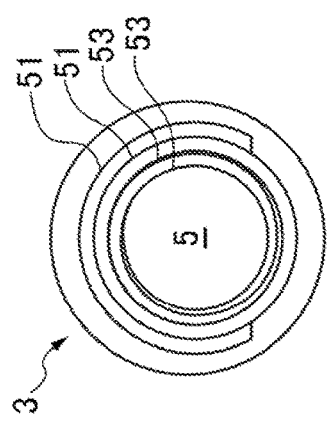
FIG. 4D is an enlarged side view illustrating a distal part in the combination of Example 3 and Example 4.
Figure 5C:
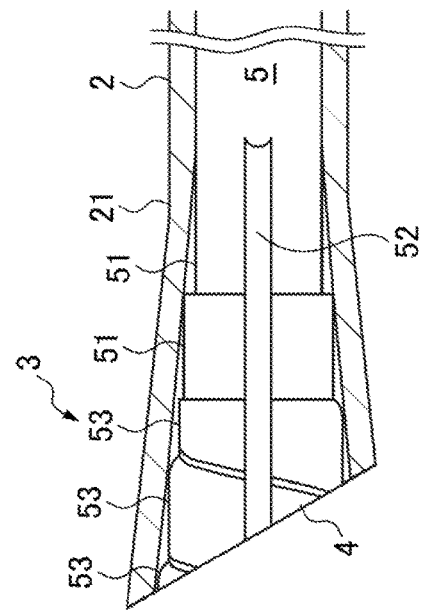
FIG. 5C is an enlarged cross-sectional view illustrating a distal part in the combination of Example 3 and Example 5.
Figure 5D:
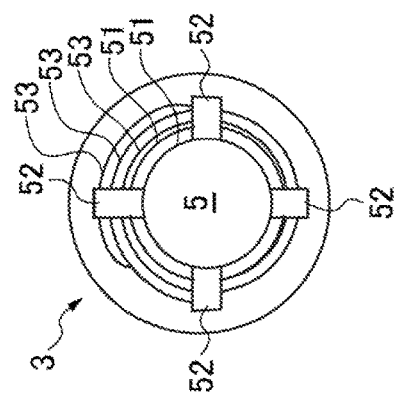
FIG. 5D is an enlarged side view illustrating a distal part in the combination of Example 3 and Example 5.
Figure 5A:
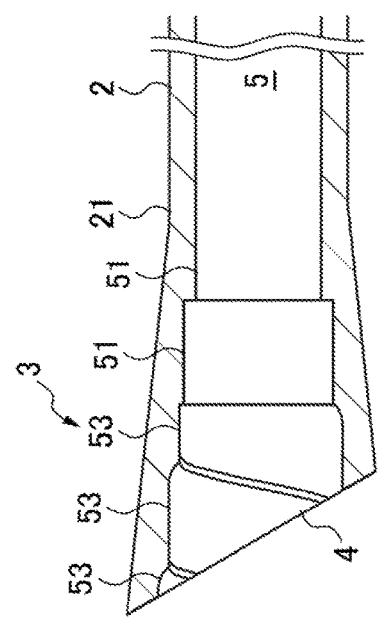
FIG. 5A is an enlarged cross-sectional view illustrating a distal part in Example 5.
Figure 5B:
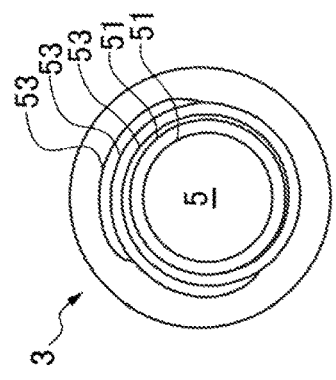
FIG. 5B is an enlarged side view illustrating a distal part in Example 5.

Here, it should be noted that, in Example 2, the suction passage 5 is narrowed in a helical shape from an opening 4 toward a shaft 2 as indicated with numerals 53 in FIGS. 3A and 3B. In the illustrated example, a conical flow channel gradually decreasing in inside diameter is formed at a section of a distal part 3 in the suction passage 5 and helical grooves are provided in an inner wall surface of the conical flow channel to form helical shape structures 53.

This causes a crushed substance of the crystalline lens (not illustrated) sucked from the opening 4 to collide with the helical shape structures 53 and thereby be more finely crushed, thus greatly improving the crushing efficiency of the tip 1. Further, the fluid containing the crushed substance of the crystalline lens is guided to the downstream side along helical grooves 55 forming the helical shape structures 53, so that the fluid, which has collided with the above-described helical shape structures 53, extremely smoothly flows out to the downstream side (the suction passage 5, the communication passage 9) without staying near the above-described structures 53.

Example 3

(Tip in which Helical Shape Structures and Guide Grooves are Arranged in a Suction Passage on a Distal Part Side)

A tip 1 in Example 3 has helical shape structures 53 that are substantially the same as those of the tip 1 in Example 2 and has guide grooves 52 as those described in Example 1 (see FIGS. 3C and 3D). This promotes the suction of fluid to a suction passage 5 and the discharge of the fluid from the suction passage 5 and also improves the crushing efficiency of the tip 1.

Example 4

(Tip in which Helical Shape Structures and Guide Grooves are Arranged in a Suction Passage on a Distal Part Side)

Example 4 includes, though not illustrated, a tip 1 which has a suction passage 5 made by combining the staircase shape structures 51 as exemplified in Example 1 and the helical shape structures 53 as exemplified in Examples 2, 3.

Concretely, the suction passage 5 is configured, at a distal part 3, to have a first section (namely, a suction side section, not illustrated) provided on an opening 4 side and a second section (namely, a discharge side section, not illustrated) provided on a first end 21 side of a shaft 2. Further, in the first section, the flow channel shape of the suction passage 5 is narrowed in a staircase shape toward the shaft 2. On the other hand, in the second section, the flow channel shape of the suction passage 5 is narrowed in a helical shape toward the shaft 2.

This configuration causes a crushed substance of the crystalline lens (not illustrated) sucked from an opening 4 to collide with wall surfaces of the staircase shape structures 51 and the helical shape structures 53 in sequence and thereby be more finely crushed, thus greatly improving the crushing efficiency of the tip 1. Further, the fluid containing the crushed substance by the helical grooves is guided to smoothly flow to the downstream side of the suction passage 5.

Example 5

Besides, Example 5 is a modification example of Example 4 and is, though not illustrated, configured such that the flow channel shape in the above-described first section described in Example 4 is narrowed in a helical shape, whereas the flow channel shape of a suction passage 5 is narrowed in a staircase shape toward a shaft 2 in the second section. Namely, Example 5 is configured such that the installation order of the staircase shape flow channel and the helical flow channel in Example 4 is made different (reversed).

The tip 1 in Example 4 or Example 5 may be provided with the guide grooves 52 as those described in Examples 1, 3. This is because the provision further promotes the suction of fluid into the suction passage 5 and the discharge of the fluid from the suction passage 5 and further improves also the crushing efficiency of the tip 1.

Further, the number of guide grooves 52 is not limited to the installation number shown in each example, but at least one guide groove 52 may be disposed. Further, as the illustrated guide grooves 52, horizontal grooves extending in parallel to the axis of the suction passage 5 are exemplified, but the guide grooves 52 are not necessarily limited to them but may be, for example, grooves inclined with respect to the axis.

INDUSTRIAL APPLICABILITY

As described above, the tip for phacoemulsification 1 according to the present invention is superior in ability to efficiently and smoothly crush and suck a crystalline lens as compared with a conventional one and has extremely high industrial utility value and industrial applicability.

EXPLANATION OF CODES

1 tip for phacoemulsification
2 shaft 3 distal part
4 opening of distal part
5 suction passage
6 thread part
7 hub
8 opening of thread part
9 communication passage
21 first end of shaft
22 second end of shaft
51 staircase shape structure
52 guide groove
53 helical shape structure

What is claimed is:

1. A tip for phacoemulsification, comprising:
a shaft having first and second ends;
a distal part arranged at the first end of the shaft and having an opening; and
a suction passage extending from the opening of the distal part to the second end of the shaft,
wherein the suction passage has, at the distal part, a first section provided on the opening side and a second section provided on the first end side of the shaft,
wherein the suction passage is narrowed in a staircase shape toward the shaft, in the first section, and
wherein the suction passage is narrowed in a helical shape toward the shaft, in the second section.

2. The tip for phacoemulsification according to claim 1, wherein one or a plurality of guide grooves leading from the opening toward the shaft are further formed in an inner wall of the suction passage.

3. A tip for phacoemulsification, comprising:
a shaft having first and second ends;
a distal part arranged at the first end of the shaft and having an opening; and
a suction passage extending from the opening of the distal part to the second end of the shaft,
wherein the suction passage has, at the distal part, a first section provided on the opening side and a second section provided on the first end side of the shaft,
wherein the suction passage is narrowed in a helical shape toward the shaft, in the first section, and
wherein the suction passage is narrowed in a staircase shape toward the shaft, in the second section.

4. The tip for phacoemulsification according to claim 3, wherein one or a plurality of guide grooves leading from the opening toward the shaft are further formed in an inner wall of the suction passage.

\* \* \* \* \*